United States Patent
Clode et al.

(10) Patent No.: US 6,326,515 B1
(45) Date of Patent: Dec. 4, 2001

(54) CARBONYLATION OF METHANOL TO ACETIC ACID WITH REMOVAL OF IMPURITIES FROM THE PRODUCT

(75) Inventors: Kirsten Everald Clode; Derrick John Watson, both of East Yorkshire (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/391,177

(22) Filed: Sep. 8, 1999

(30) Foreign Application Priority Data

Sep. 8, 1998 (GB) .................................. 9819606

(51) Int. Cl.$^7$ .................................. C07C 51/42
(52) U.S. Cl. .................. 562/608; 562/519; 562/607
(58) Field of Search .................. 562/519, 608, 562/607

(56) References Cited

U.S. PATENT DOCUMENTS

| | | |
|---|---|---|
| 3,769,177 | 10/1973 | Eubanks et al. . |
| 3,772,380 | 11/1973 | Paulik et al. . |
| 3,791,935 | 2/1974 | Eubanks et al. . |
| 4,008,131 | 2/1977 | Price . |
| 5,723,660 | * 3/1998 | Morimoto et al. . |

FOREIGN PATENT DOCUMENTS

| | | |
|---|---|---|
| 17 67 150 | 5/1972 | (DE) . |
| 0 384 652 A1 | 8/1990 | (EP) . |
| 0 391 680 A1 | 10/1990 | (EP) . |
| 0 573 189 A1 | 12/1993 | (EP) . |
| 0 616 997 A1 | 9/1994 | (EP) . |
| 0 618 183 A1 | 10/1994 | (EP) . |
| 0 618 184 A1 | 10/1994 | (EP) . |
| 0 657 386 | 6/1995 | (EP) . |
| 0 768 295 A1 | 4/1997 | (EP) . |
| 0 849 250 A1 | 6/1998 | (EP) . |
| 1 233 121 | 5/1971 | (GB) . |
| 1 234 641 | 6/1971 | (GB) . |
| 95/31426 | 11/1995 | (WO) . |
| 98/17619 | 4/1998 | (WO) . |

OTHER PUBLICATIONS

Howard et al, $C_1$ to acetyls: catalysis and process.

\* cited by examiner

Primary Examiner—Gary Geist
Assistant Examiner—Robert W. Deemie
(74) Attorney, Agent, or Firm—Nixon & Vanderhye

(57) ABSTRACT

A process for removing higher organic iodides, including hexyl iodide, from an acetic acid product obtained by carbonylating methanol and/or a reactive derivative thereof in the presence of a finite concentration of water, Group VIII noble metal catalyst, methyl iodide as co-catalyst, and optionally a catalyst promoter, which process includes the step of subjecting an aqueous composition comprising acetic acid and at least one higher organic iodide to distillation in a column, or section of a column, separating water overhead from a dry acetic acid fraction, wherein the water concentration on the feed tray of the column, or section of the column, is greater than 8% by weight and the water concentration in the head of the column, and/or section of the column, is greater than 70% by weight.

10 Claims, No Drawings

CARBONYLATION OF METHANOL TO ACETIC ACID WITH REMOVAL OF IMPURITIES FROM THE PRODUCT

The present invention relates in general to a carbonylation process for the production of acetic acid and in particular to a process for the production of acetic acid by the carbonylation of methanol and/or a reactive derivative thereof in the presence of a Group VIII noble metal catalyst, methyl iodide as co-catalyst, optionally a promoter, and a finite concentration of water.

Homogeneous liquid phase processes for the production of acetic acid by the Group VIII noble metal catalysed, alkyl halide co-catalysed reaction of carbon monoxide with methanol and/or a reactive derivative thereof are well-known. The process using rhodium as the noble metal catalyst is described in, for example, GB-A-1,233,121; EPA-0384652; and EP-A-0391680. The process using iridium as the noble metal catalyst is described in, for example, GB-A-1234121, U.S. Pat. No. 3,772,380; DE-A-1767150; EP-A061997; EP-A-0618184; EP-A-0618183; EP-A-0657386; and WO-A-95/31426. Carbonylation processes for the production of acetic acid in the presence of either a rhodium or an iridium carbonylation catalyst are operated on a commercial scale at several locations worldwide.

Howard et al in Catalysis Today, 18 (1993), 325–354 describe rhodium and iridium-catalysed carbonylation of methanol to acetic acid. The continuous rhodium-catalysed, homogeneous methanol carbonylation process is said to consist of three basic sections; reaction, purification and off-gas treatment. The reaction section comprises an agitated reactor, operated at elevated temperature and pressure, and a flash vessel. Liquid reaction composition is withdrawn from the reactor and is passed through a flashing valve to a flash tank where the majority of the lighter components of the liquid reaction composition (methyl iodide, methyl acetate and water) together with product acetic acid are vaporised. The vapour fraction is then passed to the purification section whilst the liquid fraction (comprising the rhodium catalyst in acetic acid) is recycled to the reactor (cf FIG. 2 of Howard et al). The purification section is said to comprise a first distillation column (the light ends column), a second distillation column (the drying column) and a third distillation column (the heavy ends column) (cf FIG. 3 of Howard et al). In the light ends column methyl iodide and methyl acetate are removed overhead along with some water and acetic acid. The vapour is condensed and allowed to separate into two phases in a decanter, both phases being returned to the reactor. Wet acetic acid is removed from the light ends column as a sidedraw and is fed to the drying column where water is removed overhead and an essentially dry acetic acid stream is removed from the base of the distillation zone. From FIG. 3 of Howard et al it can be seen that the overhead water stream from the drying column is recycled to the reaction section. Heavy liquid by-products are removed from the base of the heavy ends column with product acetic acid being taken as a sidestream. Simplification of the purification section by elimination of one or more distillation columns thereby economising on capital expenditure and/or operating costs of a plant has been proposed. Thus, for example our EP-A-0849250 (BP Case No. 8644) discloses a process for the production of an acetic acid process stream comprising less than 400 ppm propionic acid and less than 1500 ppm water which process comprises the steps:

(a) feeding methanol and/or a reactive derivative thereof and carbon monoxide to a carbonylation reactor in which there is maintained during the course of the process a liquid reaction composition comprising:
  (i) an iridium carbonylation catalyst;
  (ii) methyl iodide co-catalyst;
  (iii) optionally one or more promoters selected from the group consisting of ruthenium, osmium, rhenium, cadmium, mercury, zinc, gallium, iridium and tungsten;
  (iv) a finite amount of water at a concentration of less than about 8% by weight;
  (v) methyl acetate;
  (vi) acetic acid; and
  (vii) propionic acid by-product and its precursors;
(b) withdrawing liquid reaction composition from the carbonylation reactor and introducing at least a part of the withdrawn liquid reaction composition, with or without the addition of heat, to a flash zone to form a vapour fraction comprising water, acetic acid product, propionic acid by-product, methyl acetate, methyl iodide and propionic acid precursors, and a liquid fraction comprising involatile iridium catalyst, involatile optional promoter or promoters, acetic acid and water;
(c) recycling the liquid fraction from the flash zone to the carbonylation reactor;
(d) introducing the vapour fraction from the flash zone into a first distillation zone;
(e) removing from the first distillation zone at a point above the introduction point of the flash zone vapour fraction a light ends recycle stream comprising water, methyl acetate, methyl iodide, acetic acid and propionic acid precursors which stream is recycled in whole or in part to the carbonylation reactor, and
(f) removing from the first distillation zone at a point below the introduction point of the flash zone vapour fraction, a process stream comprising acetic acid product, propionic acid by-product, and less than 1500 ppm water and,
(g) if the process stream removed in step (f) comprises greater than 400 ppm propionic acid introducing said stream into a second distillation column, removing from a point below the introduction point of the stream from (f) propionic acid by-product and from a point above the introduction point of the stream from (f) an acetic acid process stream containing less than 400 ppm propionic acid and less than 1500 ppm water.

In addition to propionic acid impurity, the Group VIII noble metal catalysed, methyl iodide co-catalysed carbonylation of methanol and/or a reactive derivative thereof also produces as impurities higher organic iodides, especially organic iodides in the $C_5$–$C_7$ range, chief amongst which is hexyl iodide. Hexyl iodide forms a constant boiling azeotrope with acetic acid and hence is difficult to remove from acetic acid process streams by distillation. Unless additional non-distillative steps are taken for its removal, such as contact with a silver or mercury loaded cation exchange resin, or other adsorbent, hexyl iodide can therefore be found in significant amounts in the purified acetic acid product. This is undesirable because its presence therein can render the acetic acid unsuitable for use in certain downstream applications. Treatment with an adsorbent, for example, a metal loaded ion exchange resin carries with it an economic penalty. It would therefore be desirable to remove higher organic iodides during the distillative purification of crude acetic acid.

We have found that higher organic iodides, and in particular hexyl iodide, can be removed from their admixture with acetic acid obtained by carbonylation in a distillation column by controlling the water concentration profile in the column such that the concentrations of water on the feed tray in the column and in the head of the column are within defined limits. The excess water (over the levels previously employed) functions to azeotrope out the higher organic iodides and drive them up the column, where they are removeable overhead.

Accordingly the present invention provides a process for removing higher organic iodides, including hexyl iodide, from an acetic acid product obtained by carbonylating methanol and/or a reactive derivative thereof in the presence of a finite concentration of water, a Group VIII noble metal catalyst, methyl iodide as co-catalyst, and optionally a catalyst promoter, which process includes the step of subjecting an aqueous composition comprising acetic acid and at least one higher organic iodide to distillation in a column, or section of a column, separating water overhead from a dry acetic acid fraction, wherein the water concentration on the feed tray of the column, or section of the column, is greater than 8% by weight and/or the water concentration in the head of the column, or section of the column, is greater than 70% by weight.

The water concentration on the feed tray of the column, or section of the column, is greater than 8%, preferably greater than 10% by weight, typically from 8 to 14%, for example 10 to 14% by weight. The water concentration at the head of the column, or section of the column is greater than 70%, preferably greater than 75% by weight, typically from 70 to 85% by weight.

An advantage of controlling the water concentration profile in the distillation column, or part thereof, in the manner according to the invention is that hexyl iodide, for example, concentrations of typically about 120 ppb in the acetic acid before distillation can be reduced to 5 ppb, or less. Since pushing water up the column, or section thereof, represents an economic operating penalty the less that can be employed to achieve the desired result, the better the economics of the separation.

The process of the present invention may be operated in for example the drying column of Howard et al. In one embodiment the present invention provides a process for the production of acetic acid which process comprises the steps:
(a) feeding methanol and/or a reactive derivative thereof and carbon monoxide to a carbonylation reactor in which there is maintained during the course of the process a liquid reaction composition comprising (i) a Group VIII noble metal carbonylation catalyst, (ii) methyl iodide co-catalyst, (iii) (a) in the case of the Group VIII noble metal catalyst being rhodium, optionally one or more promoters of a type forming an iodide salt, e.g. lithium iodide, (b) in the case of the Group VIII noble metal catalyst being iridium, optionally one or more promoters selected from the group consisting of ruthenium, osmium, rhenium, cadmium, mercury, zinc, gallium, indium and tungsten, (iv) a finite amount of water (v) methyl acetate, (vi) acetic acid, (vii) higher organic iodides, including hexyl iodide, by-product, and propionic acid by-product and its precursors;
(b) withdrawing liquid reaction composition from the carbonylation reactor and introducing at least part of the withdrawn liquid reaction composition, with or without the addition of heat, to a flash zone to form a vapour fraction comprising water, acetic acid product, higher organic iodides by-product, methyl acetate, methyl iodide, propionic acid by-product and propionic acid precursors, and a liquid fraction comprising involatile Group VIII noble metal catalyst, involatile optional promoter or promoters, acetic acid and water;
(c) recycling the liquid fraction from the flash zone to the carbonylation reactor;
(d) introducing the vapour fraction from the flash zone into a first distillation zone;
(e) removing from the first distillation zone at a point above the introduction point of the flash zone vapour fraction a light ends recycle stream comprising water, methyl acetate, methyl iodide, acetic acid and propionic acid precursors which stream is recycled in whole or in part to the carbonylation reactor;
(f) removing from the first distillation zone as a sidedraw at a point below the introduction point of the flash zone vapour fraction, a stream comprising acetic acid, water, propionic acid by-product, and higher organic iodides by-product;
(g) feeding the sidedraw stream from (f) to an intermediate point in a second distillation zone wherein the water concentration on the feed tray to the column is greater than 8% by weight, and/or the water concentration at the head of the column is greater than 70% by weight;
(h) removing from the second distillation zone an overhead fraction comprising water and higher organic iodides and from a point below the feed point a fraction comprising acetic acid product and propionic acid by-product with significantly reduced amounts of higher organic iodides.

In this embodiment the water concentration on the feed tray of the column is maintained at greater than 8% by weight suitably by controlling the amount of the overhead fraction removed from the second distillation zone which, after condensing, is returned to the column as reflux. The water concentration at the head of the column is in part maintained at greater than 70% by weight in the same manner.

The overhead fraction removed from the second distillation zone in step (h) comprising water and higher organic iodides is suitably recycled as a liquid to the carbonylation reactor. In the reactor hexyl iodide is converted to heptanoic acid which presents no problems as an impurity in acetic acid at part per billion levels. Optionally, this overhead stream may be subjected to further distillative processes in order to remove the organic iodides.

Alternatively, the process of the present invention may be operated in a section of a column in which other distillative separations are also occurring, such as for example in a combined light ends/drying column or a combined light ends/drying/heavy ends column as described in the aforesaid EP-A-0849250.

Thus, in an alternative embodiment the present invention provides a process for the production of acetic acid which process comprises the steps:
(a) to (c) as hereinbefore described;
(d) introducing the vapour fraction from the flash zone into a first distillation zone, which first distillation zone incorporates an upper section wherein an aqueous composition comprising acetic acid and at least one higher organic iodide is separated into water overhead from a dry acetic acid fraction, the water concentration on the feed tray being greater than 8% by weight and the water concentration at the head of the section being greater than 70% by weight;
(e) removing from the first distillation zone an overhead vapour fraction comprising water, higher organic iodides, methyl acetate, methyl iodide, propionic acid precursors and acetic acid;
(f) condensing the overhead vapour fraction from (e), passing the condensate to a decanter wherein it is separated into a methyl iodide-rich phase and an aqueous phase, the methyl iodide-rich phase being recycled to the carbonylation reactor and the aqueous phase being divided, part being returned to the first distillation zone as reflux and the remainder being recycled to the carbonylation reactor;

(g) removing from the first distillation zone at a point below the introduction point of the flash zone vapour fraction, a process stream comprising dry acetic acid and propionic acid by-product; and (h) optionally introducing the aforesaid stream into a second distillation zone;

(i) removing from the second distillation zone a bottom fraction comprising propionic acid; and (j) removing from the second distillation zone a sidedraw fraction comprising dry acetic acid product containing less than 250 ppm propionic acid.

Methanol and/or a reactive derivative thereof, for example methyl acetate, dimethyl ether or methyl iodide, is fed to the carbonylation reactor.

A finite concentration of water typically from 0.1 to 30, suitably from 0.1 to 15, preferably from 0.5 to 10, more preferably from 1 to 6% by weight is present in the liquid reaction composition.

Water may be formed in situ in the carbonylation reaction, for example by the esterification reaction between methanol and/or reactive derivative thereof reactant and carboxylic acid product. Water may be introduced to the carbonylation reactor together with or separately from the other liquid reactants. Water may be separated from reaction composition withdrawn from the reactor and recycled in controlled amounts to maintain the required concentration in the carbonylation reaction composition.

Of the Group VIII noble metals, rhodium and iridium are preferred. The Group VIII noble metal may be present in the liquid reaction composition in any form which is soluble in the composition. It may be added to the liquid reaction composition in any form which is soluble in the composition or is convertible to soluble form. Examples of suitable rhodium-containing compounds which may be added to the liquid reaction composition include $[Rh(CO)_2Cl]_2$, $(Rh(CO)_2I)_2$, $[Rh(Cod)Cl]_2$, rhodium (III) chloride, rhodium (III) iodide, rhodium (III) acetate, rhodium dicarbonylacetylacetone, $RhCl_3(PPh_3)_3$ and $RhCl(CO)(PPh_3)_2$. Iridium is preferably used as a chloride-free compound such as a carboxylate salt, e.g. the acetate, which is soluble in one or more of the liquid reaction components, e.g. water and/or acetic acid, and so may be added as a solution therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-$$H^+$, $[Ir(CO)_2I_2]^{-H+}$, $[Ir(CH_3)I_3(CO)_2]^{31}$ $H^{3O}$, $Ir(CO)_{12}$, $IrCl_3.4H_2O$, $IrBr_3.4 H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$ and hexachloroiridic acid $H_2[IrCl_3]$, preferably chloride-free complexes of iridium such as acetates, oxalates and acetoacetates.

Preferably the concentration of the catalyst in the liquid reaction composition is in the range from 50 to 5000 ppm by weight of the metal, preferably 100 to 2500 ppm by weight of the metal.

There is employed as co-catalyst in the liquid reaction composition methyl iodide. A suitable methyl iodide concentration in the liquid reaction composition is in the range from 1 to 30% by weight, more preferably 1 to 20% by weight, for example 1 to 10% by weight.

Optionally one or more promoters may be present in the liquid reaction composition. The choice of promoter will to some extent depend upon the nature of the catalytic metal. Using iridium as catalyst the use of metal promoters is preferred. The metal promoter may suitably be one or more of osmium, rhenium, ruthenium, cadmium, mercury, zinc, gallium, iridium and tungsten. Preferably the promoter is selected from ruthenium and osmium and most preferably is ruthenium. The promoter may comprise any promoter metal-containing compound which is soluble in the liquid reaction composition. The promoter may be added to the liquid reaction composition in any suitable form which dissolves in the liquid reaction composition or is convertible to soluble form. Examples of suitable promoter metal-containing compounds include carboxylate salts, for example acetates and carbonyl complexes. Preferably chloride-free compounds are employed. Preferably the promoter metal compounds are free of impurities which provide or generate in-situ ionic iodides which may inhibit the reaction in the presence of iridium catalysts, for example alkali or alkaline earth metal or other metal salts.

Preferably, the promoter is present in an effective amount up to the limit of its solubility in the liquid reaction composition. The promoter is suitably present in the liquid reaction composition at a molar ratio of each promoter (when present): iridium in the range [0.1 to 100]:1, preferably [greater than 0.5]:1, more preferably [greater than 1]:1 and [up to 20]:1, more preferably [up to 15]:1 and yet more preferably [up to 10]: 1 The beneficial effect of a promoter such as ruthenium has been found to be greatest at the water concentration which gives the maximum carbonylation rate at any defined methyl acetate and methyl iodide concentration. A suitable promoter concentration is from 400 to 5000 ppm.

Using rhodium as the carbonylation catalyst the use of iodide promoters is preferred. Both inorganic and organic iodides may be employed. Suitable inorganic iodides include alkali metal and alkaline earth metal iodides. A preferred metal iodide is lithium iodide. The iodides may be added as such or in the form of salts, for example carboxylate salts, such as acetates, which are convertible to iodides under the carbonylation conditions. Alternatively organic iodides, suitably selected from quaternary ammonium, pyridinium, picolinium or phosphonium iodides may be employed.

The carbon monoxide feed to the carbonylation process may be essentially pure or may contain impurities such as carbon dioxide, methane, nitrogen, noble gases, water and $C_1$ to $C_4$ paraffinic hydrocarbons. The presence of hydrogen in the carbon monoxide is generally not desirable. The partial pressure of carbon monoxide in the carbonylation reaction vessel may suitably be in the range 1 to 70 barg, preferably 1 to 35 barg, more preferably 1 to 15 barg.

The total pressure of the carbonylation process is suitably in the range 10 to 100 barg. The temperature at which the carbonylation process is operated is suitably in the range 100 to 300° C., preferably in the range from 150 to 220° C. The process of the present invention will now be illustrated by reference to the following Example and comparison test.

COMPARISON TEST

There was fed to a drying column a fraction comprising acetic acid, water and hexyl iodide obtained as a sidedraw from a light ends column separating overhead a light ends recycle stream comprising water, methyl acetate, methyl iodide, acetic acid and propionic acid precursors, there being fed to the light ends column the volatile fraction comprising acetic acid product, water, higher organic iodides, methyl acetate, methyl iodide, propionic acid by-product and propionic acid precursors separated from a liquid fraction comprising involatile rhodium catalyst, acetic acid and water in a flash vessel to which was fed the liquid product obtained from the rhodium-catalysed methyl iodide co-catalysed, carbonylation of methanol in the presence of water.

Over a period of seven calendar months the concentration of water on the feed tray of the drying column was in the range from 9 to 14% by weight and the water concentration in the heads water was within the range from about 35 to 68% by weight. Over this period the concentration of hexyl iodide in the acetic acid removed from the base of the column was in the range on average from about 20 to 120 ppb.

EXAMPLE

The Comparison Test was continued for a period of over 12 months in identical fashion except that the concentration of water on the feed tray of the drying column was maintained within the range from 10 to 14%, principally 10 to 12%, by weight and the concentration of water in the heads was maintained on average in the range 70 to 85%, principally from 75 to 85% by weight. Over this period the concentration of hexyl iodide in the acetic acid removed from the base was on average less than 5 ppb.

We claim:

1. A process for removing higher organic iodides, including hexyl iodide, from an acetic acid product obtained by carbonylating methanol and/or a reactive derivative thereof in the presence of a finite concentration of water, Group VIII noble metal catalyst, methyl iodide as co-catalyst, and optionally a catalyst promoter, which process includes the step of subjecting an aqueous composition comprising acetic acid and at least one higher organic iodide to distillation in a column, or section of a column, separating water overhead from a dry acetic acid fraction, wherein the water concentration on the feed tray of the column, or section of the column, is greater than 8% by weight and the water concentration in the head of the column, or section of the column, is greater than 70% by weight.

2. A process as claimed in claim 1 wherein the water concentration on the feed tray of the column is from 8 to 14%.

3. A process as claimed in claim 1 wherein the concentration of water at the head of the column is from 70 to 85% by weight.

4. A process as claimed in claim 1 wherein the finite concentration of water is from 0.1 to 30% by weight in the liquid reaction composition.

5. A process as claimed in claim 1 wherein the Group VIII noble metal catalyst is rhodium or iridium.

6. A process as claimed in claim 5 wherein the catalyst is present in the liquid reaction composition in the range of from 50 to 5000 ppm by weight of metal.

7. A process as claimed in claim 1 wherein the promoter is a metal promoter, a inorganic iodide or organic iodide.

8. A process as claimed in claim 1 carried out under a pressure of 10 to 100 barg and a temperature of 100 to 300° C.

9. A process as claimed in claim 1 which comprises the steps:

(a) feeding methanol and/or a reactive derivative thereof and carbon monoxide to a carbonylation reactor in which there is maintained during the course of the process a liquid reaction composition comprising (i) a Group VIII noble metal carbonylation catalyst, (ii) methyl iodide co-catalyst, (iii) (a) in the case of the Group VIII noble metal catalyst being rhodium, optionally one or more promoters of a type forming an iodide salt, e.g. lithium iodide, (b) in the case of the Group VIII noble metal catalyst being iridium, optionally one or more promoters selected from the group consisting of ruthenium, osmium, rhenium, cadmium, mercury, zinc, gallium, indium and tungsten, (iv) a finite amount of water (v) methyl acetate, (vi) acetic acid, (vii) higher organic iodides, including hexyl iodide, by-product, and propionic acid by-product and its precursors;

(b) withdrawing liquid reaction composition from the carbonylation reactor and introducing at least part of the withdrawn liquid reaction composition, with or without the addition of heat, to a flash zone to form a vapour fraction comprising water, acetic acid product, higher organic iodides by-product, methyl acetate, methyl iodide, propionic acid by-product and propionic acid precursors, and a liquid fraction comprising involatile Group VIII noble metal catalyst, involatile optional promoter or promoters, acetic acid and water;

(c) recycling the liquid fraction from the flash zone to the carbonylation reactor;

(d) introducing the vapour fraction from the flash zone into a first distillation zone;

(e) removing from the first distillation zone at a point above the introduction point of the flash zone vapour fraction a light ends recycle stream comprising water, methyl acetate, methyl iodide, acetic acid and propionic acid precursors which stream is recycled in whole or in part to the carbonylation reactor;

(f) removing from the first distillation zone as a sidedraw at a point below the introduction point of the flash zone vapour fraction, a stream comprising acetic acid, water, propionic acid by-product, and higher organic iodides by-product;

(g) feeding the sidedraw stream from (f) to an intermediate point in a second distillation zone wherein the water concentration on the feed tray to the column is greater than 8% by weight, and the water concentration at the head of the column is greater than 70% by weight;

(h) removing from the second distillation zone an overhead fraction comprising water and higher organic iodides and from a point below the feed point a fraction comprising acetic acid product and propionic acid by-product with significantly reduced amounts of higher organic iodides.

10. A process as claimed in claim 1 which comprises the steps of:

(a) feeding methanol and/or a reactive derivative thereof and carbon monoxide to a carbonylation reactor in which there is maintained during the course of the process a liquid reaction composition comprising (i) a Group VIII noble metal carbonylation catalyst, (ii) methyl iodide co-catalyst, (iii) (a) in the case of the Group VIII noble metal catalyst being rhodium, optionally one or more promoters of a type forming an iodide salt, e.g. lithium iodide, (b) in the case of the Group VIII noble metal catalyst being iridium, optionally one or more promoters selected from the group consisting of ruthenium, osmium, rhenium, cadmium, mercury, zinc, gallium, indium and tungsten, (iv) a finite amount of water (v) methyl acetate, (vi) acetic acid, (vii) higher organic iodides, including hexyl iodide, by-product, and propionic acid by-product and its precursors;

(b) withdrawing liquid reaction composition from the carbonylation reactor and introducing at least part of the withdrawn liquid reaction composition, with or without the addition of heat, to a flash zone to form a vapour fraction comprising water, acetic acid product, higher organic iodides by-product, methyl acetate, methyl iodide, propionic acid by-product and propionic acid precursors, and a liquid fraction comprising involatile Group VIII noble metal catalyst, involatile optional promoter or promoters, acetic acid and water;

(c) recycling the liquid fraction from the flash zone to the carbonylation reactor;

(d) introducing the vapour fraction from the flash zone into a first distillation zone, which first distillation zone incorporates an upper section wherein an aqueous composition comprising acetic acid and at least one higher organic iodide is separated into water overhead from a dry acetic acid fraction, the water concentration on the feed tray being greater than 8% by weight and the water concentration at the head of the section being greater than 70% by weight;

(e) removing from the first distillation zone an overhead vapour fraction comprising water, higher organic iodides, methyl acetate, methyl iodide, propionic acid precursors and acetic acid;

(f) condensing the overhead vapour fraction from (e), passing the condensate to a decanter wherein it is separated into a methyl iodide-rich phase and an aqueous phase, the methyl iodide-rich phase being recycled to the carbonylation reactor and the aqueous phase being divided, part being returned to the first distillation zone as reflux and the remainder being recycled to the carbonylation reactor;

(g) removing from the first distillation zone at a point below the introduction point of the flash zone vapour fraction, a process stream comprising dry acetic acid and propionic acid by-product; and (h) optionally introducing the aforesaid stream into a second distillation zone;

(i) removing from the second distillation zone a bottom fraction comprising propionic acid; and (j) removing from the second distillation zone a sidedraw fraction comprising dry acetic acid product containing less than 250 ppm propionic acid.

* * * * *